US011872067B2

(12) United States Patent
Rieger et al.

(10) Patent No.: US 11,872,067 B2
(45) Date of Patent: Jan. 16, 2024

(54) PROJECTION MAPPING OF RADIATION SUITES

(71) Applicant: Varian Medical Systems, Inc., Palo Alto, CA (US)

(72) Inventors: Rachel Rieger, Redwood City, CA (US); Nitin Mangi, Hayward, CA (US); Roberto Luevano, Aptos, CA (US); Ross Hannibal, Saratoga, CA (US)

(73) Assignee: Varian Medical Systems, Inc., Palo Alto, CA (US)

( * ) Notice: Subject to any disclaimer, the term of this patent is extended or adjusted under 35 U.S.C. 154(b) by 298 days.

(21) Appl. No.: 17/009,924

(22) Filed: Sep. 2, 2020

(65) Prior Publication Data
US 2020/0405250 A1    Dec. 31, 2020

Related U.S. Application Data

(63) Continuation of application No. 15/720,092, filed on Sep. 29, 2017, now Pat. No. 10,842,454.

(51) Int. Cl.
*A61M 21/00* (2006.01)
*A61B 6/00* (2006.01)
(Continued)

(52) U.S. Cl.
CPC .............. *A61B 6/462* (2013.01); *A61B 5/055* (2013.01); *A61B 5/7296* (2013.01);
(Continued)

(58) Field of Classification Search
CPC .............. A61M 21/02; A61M 21/0094; A61M 2021/0027; A61M 2021/005; A61M 2205/59
See application file for complete search history.

(56) References Cited

U.S. PATENT DOCUMENTS 3,720,817 A * 3/1973 Dinwiddie ............... H05G 1/44
700/89
7,823,306 B1 11/2010 Kersten et al.
(Continued)

FOREIGN PATENT DOCUMENTS

JP    2012085915 A  *  5/2012  .......... A61M 121/00

OTHER PUBLICATIONS

Kurvilla, "Pirate-themed CT scanner helps New York City kids find calm waters before tests," New York Daily News, Aug. 24, 2013, 6 pages.
(Continued)

*Primary Examiner* — Samuel G Gilbert
(74) *Attorney, Agent, or Firm* — Harness, Dickey & Pierce, P.L.C.

(57) ABSTRACT

A radiation suite includes a room having a floor, a ceiling, and one or more walls, a radiation system including a gantry enclosing a radiation source and a couch, and an image projection system operable to project an image on a projection surface on at least a portion of the gantry and/or the couch, providing a calming environment for a patient to relax. The image projection system comprises a computer and one or more projectors operably controlled by the computer. The computer comprises a mapping software operable to map an image file to the projection surface. The one or more projectors are operable to project the mapped image file on the projection surface.

18 Claims, 3 Drawing Sheets

(51) Int. Cl.
*A61N 5/10* (2006.01)
*A61B 90/00* (2016.01)
*G01N 21/3563* (2014.01)
*A61B 6/04* (2006.01)
*A61B 5/055* (2006.01)
*A61N 5/06* (2006.01)
*A61B 5/00* (2006.01)
*A61B 5/11* (2006.01)
*A61B 5/08* (2006.01)

(52) U.S. Cl.
CPC ............ *A61B 6/0407* (2013.01); *A61B 90/36* (2016.02); *A61M 21/00* (2013.01); *A61N 5/0618* (2013.01); *A61N 5/1001* (2013.01); *A61N 5/1049* (2013.01); *A61N 5/1068* (2013.01); *G01N 21/3563* (2013.01); *A61B 5/0816* (2013.01); *A61B 5/11* (2013.01); *A61B 5/1113* (2013.01); *A61B 5/486* (2013.01); *A61M 2021/005* (2013.01); *A61M 2021/0027* (2013.01); *A61M 2205/581* (2013.01); *A61M 2205/582* (2013.01); *A61M 2230/42* (2013.01); *A61N 5/1081* (2013.01); *A61N 2005/1061* (2013.01); *A61N 2005/1092* (2013.01)

(56) References Cited

U.S. PATENT DOCUMENTS

| | | | |
|---|---|---|---|
| 9,232,928 | B2 | 1/2016 | Mostafavi |
| 2007/0273845 | A1* | 11/2007 | Birmingham ........ G03B 21/008 353/101 |
| 2012/0157758 | A1 | 6/2012 | Dietz |
| 2014/0121453 | A1 | 5/2014 | Maslowski et al. |
| 2014/0171729 | A1* | 6/2014 | Bourne ................ G16H 10/60 600/27 |

OTHER PUBLICATIONS

Sansum Clinic, "Virtual Reality Goggles Reduce Pain and Fear," Jan. 25, 2017, 5 pages.
Bush, "Stanford University—Anesthesia Alternative," 2017, retrieved from www.vimeo.com on Jul. 7, 2017.
European Society for Radiotherapy and Oncology (ESTRO), "Watching movies can replace general anesthesia for kids with cancer having radiotherapy," May 8, 2017, 3 pages.

* cited by examiner

PROJECTION MAPPING OF RADIATION SUITES

RELATED APPLICATIONS

This application is a continuation of U.S. application Ser. No. 15/720,092 filed Sep. 29, 2017 entitled "PROJECTION MAPPING OF RADIATION SUITES," the disclosures of all of which are herein incorporated by reference in their entirety.

TECHNICAL FIELD

Embodiments of this disclosure relate generally to radiation systems and methods. In particular, various embodiments of a system and method for providing a calming environment in a radiation suite to relax a patient during treatment or imaging are described.

BACKGROUND

Patients undergoing radiation therapy or imaging can be nervous and fearful since a linear accelerator (LINAC) or radiation machine can be intimidating, especially to children. A fearful patient has a higher chance of moving during treatment or imaging because they are not in a relaxed state. Frequently, children are anesthetized during treatment because they are too nervous to hold still during the procedure.

Radiation therapists spend a significant amount of time in setting up a patient for treatment. If the patient moves, the therapist commonly will have to reimage the patient and adjust their position. This process is time consuming and difficult to solve because it interfaces with the human being treated, which is unpredictable.

Accordingly, there exists a need for methods and systems of providing a calming environment in which a patient is surrounded by a relaxing augmented reality. An immersive experience can create an emotional impact on the patient, reduce the fear and anxiety of the patient, and thus prevent the patient from moving during imaging, treatment, or patient setup.

SUMMARY

Provided herein is a system and method of projection mapping images or videos on a radiation machine and/or a treatment room to create a calming environment for a patient to relax during setup and treatment. A visual projection mapped stimulus, incorporated with calming sounds and smells related to the visual stimulus, can create an immersive distraction from the fact that the patient is being treated for cancer.

One or more projectors such as ultra-short throw projectors may be mounted in a treatment room to cover the radiation machine and the walls, floor, and/or ceiling of the treatment room with a mapped image or video. The number and location of projectors is dependent on the size and geometry of the treatment room.

A scanner such as an infrared 3D scanner may also be mounted in the treatment room. The scanner and corresponding software can automatically detect the contours and geometry of the treatment room and the radiation machine. Once the contour and geometry of the treatment room and the radiation machine are provided, a mapping software run in a computer can adjust or map a variety of preset images or videos to the projection surface on the treatment room and the radiation machine. The image and video content can be chosen or altered based on the environment that can calm a particular patient.

The scanner and corresponding software can determine a dynamic object in space. For example, the scanner and corresponding software can determine the gantry rotation and/or couch movement, and the mapping software run in the computer may provide compensation in projection mapping the rotating gantry and moving couch. The scanner and corresponding software can detect the location of the patient in the room, which can be used for visual feedback. By way of example, when the patient is detected walking through an augmented water-filled floor, the projected images or videos can be altered to produce e.g. water moving around the patient's feet. The type of feedback may be specific to the video and image content.

A projector may also be mounted in the treatment room to project images or videos in the direction of a patient's viewpoint during treatment since this is the position the patient remains in for the longest time. The images or videos can be used as a distraction to keep the patient relaxed. Alternatively, the projected images or videos can be used for visual gating learning or feedback during treatment. By way of example, a video can be selected to help the patient look in a particular direction or breathe at a particular rate.

In one aspect of the disclosure, a radiation suite is provided. The radiation suite includes a room having a floor, a ceiling, and one or more walls, a radiation system including a gantry enclosing a radiation source and a couch, and an image projection system operable to project an image on a projection surface on at least a portion of the radiation system, providing a calming environment for a patient. The image projection system comprises a computer and one or more projectors operably controlled by the computer. The computer comprises a mapping software operable to map an image file to the projection surface. The one or more projectors are operable to project the mapped image file on the projection surface.

In some embodiments, the radiation suite may further include a scanner. The computer comprises scanning software. The scanner and scanning software are operable to detect the geometry of the radiation system and/or the room and provide data about the geometry to the mapping software for projection mapping.

In some embodiments, the scanner and the scanning software may be operable to detect movement of the gantry and/or couch of the radiation system which causes a change of the projection surface, and the mapping software is operable to dynamically alter the image file in response to the change of the projection surface caused by the movement of the gantry and/or couch.

In a specific embodiment, the gantry of the radiation system is generally C-shaped rotatable about a horizontal axis.

In another specific embodiment, the gantry comprises a ring gantry having a bore configured to receive at least a portion of the patient supported by the couch. The image projection system may comprise an additional projector operably controlled by the computer to project an image file to at least a portion of the surface defining the bore in a direction of the viewpoint of the patient supported by the couch. The image projected on the surface of the bore may be adapted to relax the patient, or adapted to prompt the patient to maintain a desired physiological movement pattern. The ring gantry may enclose a radiation source operable to produce therapeutic radiation for treatment and/or operable to produce radiation for imaging.

In some embodiments, the radiation suite may further include an audio system operably controlled by the computer to provide a soundtrack related to the image content and/or a gaseous system operably controlled by the computer to provide a scent related to the image content.

In some embodiments, the projection surface may further comprise at least a portion of the floor, the ceiling, and/or the one or more walls of the room. The scanner and the scanning software may be operable to detect movement of a patient walking on the floor which causes a change of the projection surface. The mapping software may be operable to alter the image file in response to the change of the projection surface caused by the walking patient, providing a dynamic interaction between the walking patient and the projected image. The radiation suite may further include an audio system operably controlled by the computer to concurrently provide a soundtrack related to the altered image content, and/or a gaseous system operably controlled by the computer to concurrently provide a scent related to the altered image content.

In another aspect of the disclosure, a method of calming a patient in a radiation suite is provided. According to the method, an image file containing contents that calms a patient is mapped to at least a portion of a radiation system in the radiation suite. The mapped image file is then projected to the at least portion of the radiation system, providing a calming environment for the patient.

In some embodiments, the mapping step may comprise mapping the image file to at least a portion of the floor, ceiling, and/or the one or more walls of the room, and the projecting step may comprise projecting the mapped image file to the at least portion of the floor, ceiling, and/or the one or more walls of the room.

In some embodiments, the method may further comprise detecting movement of the patient walking in the room, altering the image file in response to the movement of the patient walking in the room, and projecting the altered image file to the at least portion of the floor, ceiling, and/or the one or more walls of the room.

In some embodiments, the method may comprise providing a sound and/or a scent related to the image content during projection of the mapped image file.

In some embodiments, the radiation system may comprise a gantry enclosing a radiation source and a couch, and the method may further comprise detecting movement of the gantry and/or couch, altering the image file in response to the movement of the gantry and/or couch, and projecting the altered image file to the at least portion of the radiation system.

In some embodiments, the radiation system may comprise a ring gantry and a couch. The ring gantry may have a bore configured to receive at least a portion of the patient supported by the couch, and the method may further comprise projecting an additional image file to at least a portion of the surface defining the bore in a direction of the viewpoint of the patient supported by the couch. The image file projected on the surface of the bore may be adapted to relax the patient or to prompt the patient to maintain a desired physiological movement pattern.

This Summary is provided to introduce selected embodiments in a simplified form and is not intended to identify key features or essential characteristics of the claimed subject matter, nor is it intended to be used as an aid in determining the scope of the claimed subject matter. The selected embodiments are presented merely to provide the reader with a brief summary of certain forms the invention might take and are not intended to limit the scope of the invention.

Other aspects and embodiments of the disclosure are described in the section of Detailed Description.

BRIEF DESCRIPTION OF THE DRAWINGS

These and various other features and advantages will become better understood upon reading of the following detailed description in conjunction with the accompanying drawings and the appended claims provided below, where:

DETAILED DESCRIPTION

Various embodiments of projection mapping a radiation suite are described. It is to be understood that the disclosure is not limited to the particular embodiments described. An aspect described in conjunction with a particular embodiment is not necessarily limited to that embodiment and can be practiced in any other embodiments.

Various embodiments are described with reference to the figures. It should be noted that some figures are not necessarily drawn to scale. The figures are only intended to facilitate the description of specific embodiments, and are not intended as an exhaustive description or as a limitation on the scope of the disclosure. Further, in the figures and description, specific details may be set forth in order to provide a thorough understanding of the disclosure. It will be apparent to one of ordinary skill in the art that some of these specific details may not be employed to practice embodiments of the disclosure. In other instances, well known components may not be shown or described in detail in order to avoid unnecessarily obscuring embodiments of the disclosure.

All technical and scientific terms used herein have the meaning as commonly understood by one of ordinary skill in the art unless specifically defined otherwise. As used in the description and appended claims, the singular forms of "a," "an," and "the" include plural references unless the context clearly dictates otherwise. The term "or" refers to a nonexclusive "or" unless the context clearly dictates otherwise. The term "first" or "second" etc. may be used to distinguish one element from another. The use of the term "first" or "second" should not be construed as in any particular order unless the context clearly dictates otherwise. Further, the singular form of "first" and "second" include plural references unless the context clearly dictates otherwise.

As used herein, the term "image" includes either a still image or a video feed, and includes either a pictorial image and/or a text image.

Disclosed herein is a system and method for projection mapping a radiation suite to provide an augmented reality or a calming environment. An image file can be projection mapped to a three-dimensional surface on a radiation system and/or room. The projected images or videos are particularly suited for calming or relaxing the patient, reducing fear and anxiety of the patient, and thus preventing or reducing the patient movement during setup and treatment or imaging. The image file can be dynamically altered in response to e.g.

the changing location of the patient walking in the room or in response to the movement of the gantry and/or couch of the radiation system. A soundtrack and/or a scent related to the image content may be provided concurrently to create a greater emotional impact on the patient.

Figure 1:
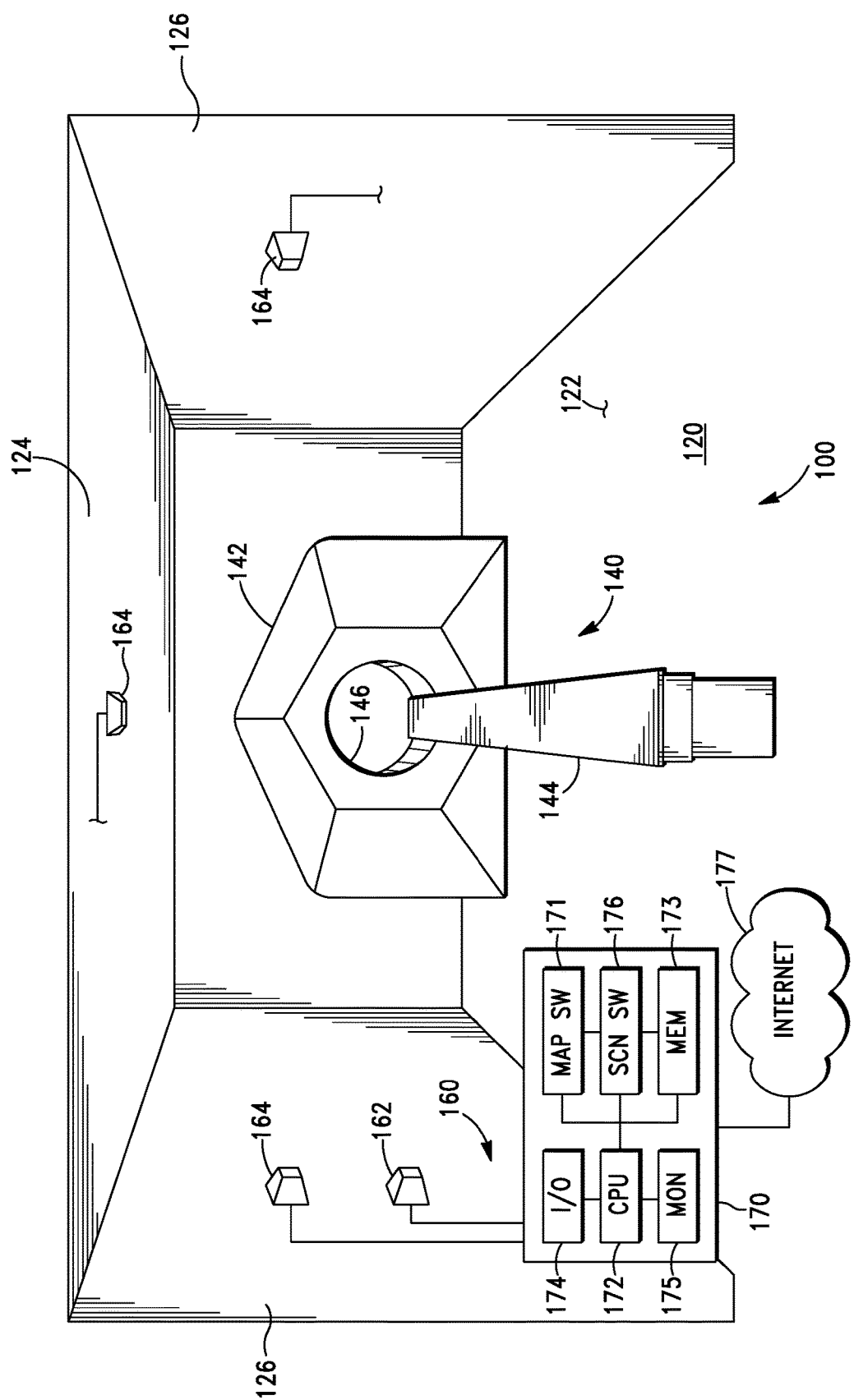
FIG. 1 illustrates an exemplary radiation suite including a radiation system and an image projection system according to embodiments of the disclosure.

FIG. 1 schematically illustrates a radiation suite 100 according to embodiments of the disclosure. As shown, the radiation suite 100 includes a room 120, a radiation system 140, and an image projection system 160. The image projection system 160 is operable to map an image file to a projection surface on the radiation system 140 and/or the room 120 and project the mapped image file on the projection surface, creating a calming environment for a patient. The radiation suite 100 may also include a scanner 162 operable to measure the room geometry for projection mapping or to track movement of the patient and/or radiation system for creating a dynamic interaction between the projected image and a moving object.

The room 120 may include a floor 122, a ceiling 124, and one or more walls 126. At least a surface portion of the floor 122, ceiling 124, and walls 126 may constitute a projection surface displaying an image projected by the image projection system 160. In some embodiments, all of the exposed surfaces of the floor 122, ceiling 124, and walls 126 may constitute a projection surface displaying an image projected by the image projection system 160. As shown, the room 120 may include planar surfaces such as flat floor 122, flat ceiling 124, flat walls 126. The room 120 may also include curved or angled surfaces such as a curved ceiling portion. The room 120 may further include non-coplanar surfaces such as adjoining walls 126, adjoining ceiling 124 and walls 126, adjoining floor 122 and walls 126 etc. The image projection system 160, as will be described in greater detail below, may map an image file to the complex three-dimensional display surfaces of the room 120, and the radiation system 140 as will be described below, such that the image projected on the display surfaces does not exhibit optical distortion. As used in the following description and appended claims, the term "projection surface" includes reference to a combination of a plurality of surfaces of various shapes, sizes, geometries, and contours, which collectively constitute a complex three-dimensional display surface.

The radiation system 140 may be a treatment system, an imaging system, or a simulation system. The radiation system 140 may be an x-ray radiation system, a gamma-ray radiation system, or a proton or heavy ion radiation system and so forth. The imaging system may be any kind of modalities including computed tomography (CT), magnetic resonance (MR), single photon emission computed tomography (SPECT), and so forth. The radiation system 140 may be a system that can perform both treatment and imaging. Indeed, the principles and inventive ideas described in the disclosure can apply to any kind of radiation systems. Further, it will be appreciated by one of ordinary skill in the art that the principles and inventive ideas can also apply to non-radiation medical procedures and/or facilities such as a doctor's office.

The exemplary radiation system 140 shown in FIG. 1 includes a gantry 142 and a couch 144. The gantry 142 may enclose a radiation source (not shown) producing radiation and various components or devices modulating and measuring the properties of the radiation produced. The couch 144 supports a patient during irradiation. As shown, the gantry 142 may be a ring gantry, which includes a bore 146 for receiving at least a portion of the patient. A radiation source may be enclosed inside the ring gantry 142 and rotated about an isocenter. In some embodiments, the gantry may be in the form of a rotatable C-arm, which may rotate a radiation source mounted inside the gantry about an isocenter. In alternative embodiments, the gantry may be in the form of a robotic arm, carrying and moving a radiation source in multiple motion degrees of freedom. The couch 144 may also be moved in multiple motion degrees of freedom as well-known in the art.

The gantry 142 and the couch 144 may include complex three-dimensional surfaces, including planar, curved, angled surfaces of various shapes and sizes, non-coplanar, non-continuous surfaces (bore in the gantry), and linear, arcuate or circular edges, and so forth. For example, the front surface of the gantry 142 may include a combination of planar, curved or angled surfaces, non-coplanar, non-continuous surfaces, and linear, arcuate, and circular edges. The front or top surface of the couch 144 may also include a combination of planar and curved surfaces of various shapes and sizes, and linear and arcuate edges. In embodiments of the disclosure, at least a surface portion of the gantry 142 and/or the couch 144 may constitute a projection surface displaying an image projected by the image projection system 160. In some embodiments, all of the exposed surface of the gantry 142 and the couch 144 may constitute a projection surface displaying an image projected by the image projection system 160. As described above, the room 120 may also include complex three-dimension surface portions. The image projection system 160, as will be described in greater detail below, may map an image file to the complex three-dimensional projection surface on the radiation system and/or the room such that the projected image matches the structural features or geometry of the projection surface and does not exhibit optical distortion.

Still referring to FIG. 1, the image projection system 160 is operable to map an image file to at least a surface portion of the radiation system 140, a surface portion of the room 120, or combined surface portions of the radiation system 140 and room 120, which constitutes a complex three-dimensional projection surface. The image projection system 160 may include a computer 170, and one or more projectors 164 operably connected with the computer 170. The computer 170 executes a mapping software 171, which functions to map an image file to a selected projection surface on the radiation system 140 and/or the room 120. The one or more projectors 164, which may be controlled by the computer 170, are operable to project the mapped image file to the selected projection surface.

The computer 170 may be a general purpose or special purpose computer, and may include a processor 172, a memory 173, input/output devices 174, a monitor and user interface 175, and various ports (not shown) for receiving and sending data signals between the computer 170 and projectors 164 and/or scanner 162. The computer 170 may be operably connected with the projectors 164 and/or scanner 162 wirelessly or via a connector cable such as HDMI cable, USB cable, fiber-optic cable, or the like. The computer 170 can be connected to the Internet 177, e.g. to an image content provider for purchasing or downloading image data files. Alternatively, various image data files may be locally stored in the memory 173 of the computer 170 or stored in a content server which may be accessed by the computer 170. The computer 170 may include software necessary to perform various functions, including a projection mapping software 171 to be executed by a user through the user interface 175.

According to embodiments of the disclosure, the image data file to be projection mapped may include all kinds of calming images. By way of example, images of a waterfall and/or mountain scenery may have a calming effect on some patients. Some gardens may find gardens and/or rain forests more relaxing. To many children, images of animals, birds, fish, space, or the like may be more effective in distracting them from their treatment or imaging by a radiation machine. In some embodiments, an image file may include a plurality of image portions which collectively form a theme having an emotional impact on the patient. For example, an image file may include image portions to be projected to the floor, ceiling, and walls of the room 120, collectively creating a background e.g. a calm lake surrounded by a scenery mountain and waterfalls under a blue sky, and image portions to be projected to the radiation system 140 creating an appearance or illusion of e.g. a boat. A library of various image files of different categories can be made available for a patient to select before treatment or imaging, and a particular selected image file may be mapped and projected to the radiation suite for the particular patient.

The image file may include still images such as still pictures, texts photographs, or moving images such as video clips, movies, and so forth. The image may contain pictorial images and/or texts providing information such as the patient's name, hospital name and logo etc. Depending on the nature of the projected images, sounds and/or smells may be added or simultaneously added with the projected images to enhance the patient's sensory experience or make the projected illusion more realistic. The sounds can be added by a separate audio system (not shown), which may be coupled to and controlled by the computer 170, or an audio system built into the projector 164 or computer 170. The smells can be introduced by a gaseous system (not shown) controlled by the computer 170.

The mapping software 171 is operable to map an image file to a selected projection surface on the radiation system 140 and/or room 120, which may have complex, three-dimensional contour or geometry. By using a mapping software, the projected image can be mapped or aligned or matched to the complex contour or geometry of the projection surface without or with reduced optical distortion. As will be described in greater detail below, the mapping software 171 may also alter an image file in response to movement of a patient walking in the room and/or a rotating gantry or moving couch, providing a dynamic interaction between the moving object and the projected image. The mapping software 171 may be loaded to the computer 170 via a computer readable medium such as a CD-ROM, flash drive, or other external memory medium, or downloaded through the Internet 177.

The mapping software 171 run by the computer 170 can be a commercially available mapping software or custom created. Various projection mapping software are commercially available, including MadMapper® developed by GarageCube SA of Switzerland, TouchDesigner® developed by Derivative of Canada, VPT 7 developed by HC Gilje of Norway, and so forth. The mapping software 171 may be executed by the processor 172 via the user interface and monitor 175. Briefly and in general, after a projection surface on the radiation system 140 and/or room 120 is determined and an image file chosen or created, the mapping software 171 can be run by the processor 172 via the user interface 175 to map the image file to the projection surface, or to align the projected image with various geometric features of the projection surface including the shape, size, contour, or position of the projection surface, allowing the projected image to properly match the geometry and contour of the projection surface without showing or with reduced visual or optical distortion. The mapping steps or procedures by the mapping software 171 may involve warping, masking, edging, constraining, splitting, or blending of the image or other tools such as rotating, scaling, skewing, positioning, and so forth, depending on the mapping software used. The coordinates of the radiation system 140 and the room 120 in relation to the projectors 164 may be provided to the mapping software 171 for mapping. Adjustments to the projectors 164 including their orientations can be made manually or by remote control during the mapping process. The properly mapped image file may be stored in the memory 173 of the computer 170. The mapped image file may be fed to the projectors 164 and projected to the projection surface on the radiation system 140 and/or room 120. Alternatively, the mapped image file may be saved in a memory device such as a CD, USB drive or the like, which can be inserted into a port in the projectors for projection.

The one or more projectors 164, which are communicably connected with and controlled by the computer 170, are operable to project a mapped image file to the selected projection surface on the radiation system 140 and/or the room 120. Projectors are well-known in the art. Briefly and in general, the projectors 164 contain optical, mechanical, and electrical components or circuitry necessary to project an image file. In some embodiments of the disclosure, short throw or ultra-short throw projectors are used. Short throw or ultra-short throw projectors allow projection of big images in tight spaces. The term "throw" in projector terminology refers to the distance between the projector lens and the projection surface. A short throw projector has a small throw ratio, or a ratio of the throw to the width of the projection surface, generally less than 1. An ultra-short throw projector has a throw ratio generally less than 0.4. Various short throw and ultra-short throw projectors are commercially available. One example of the projectors 164 is LG PF1000U ultra-short throw projector manufactured by LG of Korea.

The location and number of the projectors 164 depend on the size and geometry of the selected projection surface on the radiation system 140, and/or the projection surface on the floor 122, the ceiling 124, and the walls 126 of the room 120. In situations where one projector cannot cover all of the selected projection surface on the radiation system 140 and/or the room 120, several projectors may be used. For example, several projectors 164 may be mounted on the walls 126, the ceiling 124, and the floor 122 to map the entire surface of the radiation suite 100 including the radiation system 140. In such situations, mapping steps or processes using the mapping software 171 can be performed for all of the projectors 164, and the projection of image files by different projectors 164 can be coordinated.

Still referring to FIG. 1, in some embodiments, the image projection system 160 may include a scanner 162 operable to measure the room 120, the radiation system 140, and other objects in the room. The measured information about the coordinates, geometry, or contour of the room 120, the radiation system 140 or other objects in the room 120 can be used by the mapping software 171 in projection mapping an image file to the radiation system and/or the room. In situations where one scanner 162 cannot cover all of the selected projection surface on the radiation system 140 and/or the room 120, several scanners may be used.

The scanner 162 may be communicably connected with the computer 170 wirelessly or via a connector cable and controlled by the computer 170. The scanner 162 may scan the room 120 and send the scanned data to the computer 170 for processing. The computer 170 may include a suitable scanning software 176 processing the scanned data and reconstructing a spatial or three-dimensional configuration representative of the contour or geometry of the room 120, the radiation system 140 or other object in the room 120, to be used by the mapping software 171 in projection mapping an image file.

Various kinds of optical or laser scanners are known in the art and commercially available. One example of the scanner 162 is an infrared (IR) 3D scanner. Briefly and in general, an IR scanner may include an infrared light source, a scanning optics, and a photodetector or light sensor. A light beam emitted from the light source can be rotated or steered by the optics to optically scan the room and the radiation system and other objects in the room. The light beam reflected back from the various objects can be detected by the photodetector, which provides output signal data. The scanner 162 may collect a variety of data points with respect to the room 120, the radiation system 140 and other objects in the room 120, including distance information for each object in its surrounding environment, a grey scale value (i.e., a measure of the intensity of light) for each distance measurement value, and coordinates (e.g., x, y, and z) for each distance measurement value. The collected data are sent to the computer 170 and processed by a scanning software 176 to generate a three dimensional (3D) reconstructed image of the scanned environment with measurements.

In some embodiments, the scanner 162 and the scanning software 176 run in the computer 170 may detect a dynamic object in the room, and the mapping software 171 can compensate for movement of the dynamic object in projection mapping an image file. For example, the scanner 162 and the scanning software 176 may operate to track movement of a patient walking in the room or of the rotating gantry and/or moving couch, which may alter the projection surface in the radiation suite. In response, the mapping software 171 may alter the image file, providing a dynamic interaction between the moving object and the projected image. The image file may be altered by e.g. intermixing with another image file to create a composite image file.

By way of example, the scanner 162 and scanning software 176 run in the computer 170 may detect in real time a patient walking through an augmented water-filled floor 122. In response, the mapping software 171 may alter the projected image or video by e.g. intermixing another image file or an overlay to create a composite image file. The projectors 164 project the composite image file, creating a projected image e.g. water moving around the patient's feet. Sounds of moving water may be added concurrently to enhance the patient's sensory experience or make the projected illusion more realistic. In another example, the scanner 162 and scanning software 176 run in the computer 170 may detect in real time the gantry rotating in an augmented star- and/or planet-filled space. In response to rotation of the gantry, the mapping software 171 may alter the image file or create a composite image file, projecting e.g. a shooting star passing the gantry. It should be noted that the above examples are provided for illustration. The type of feedback may be specific to the video and image contents.

Figure 2:
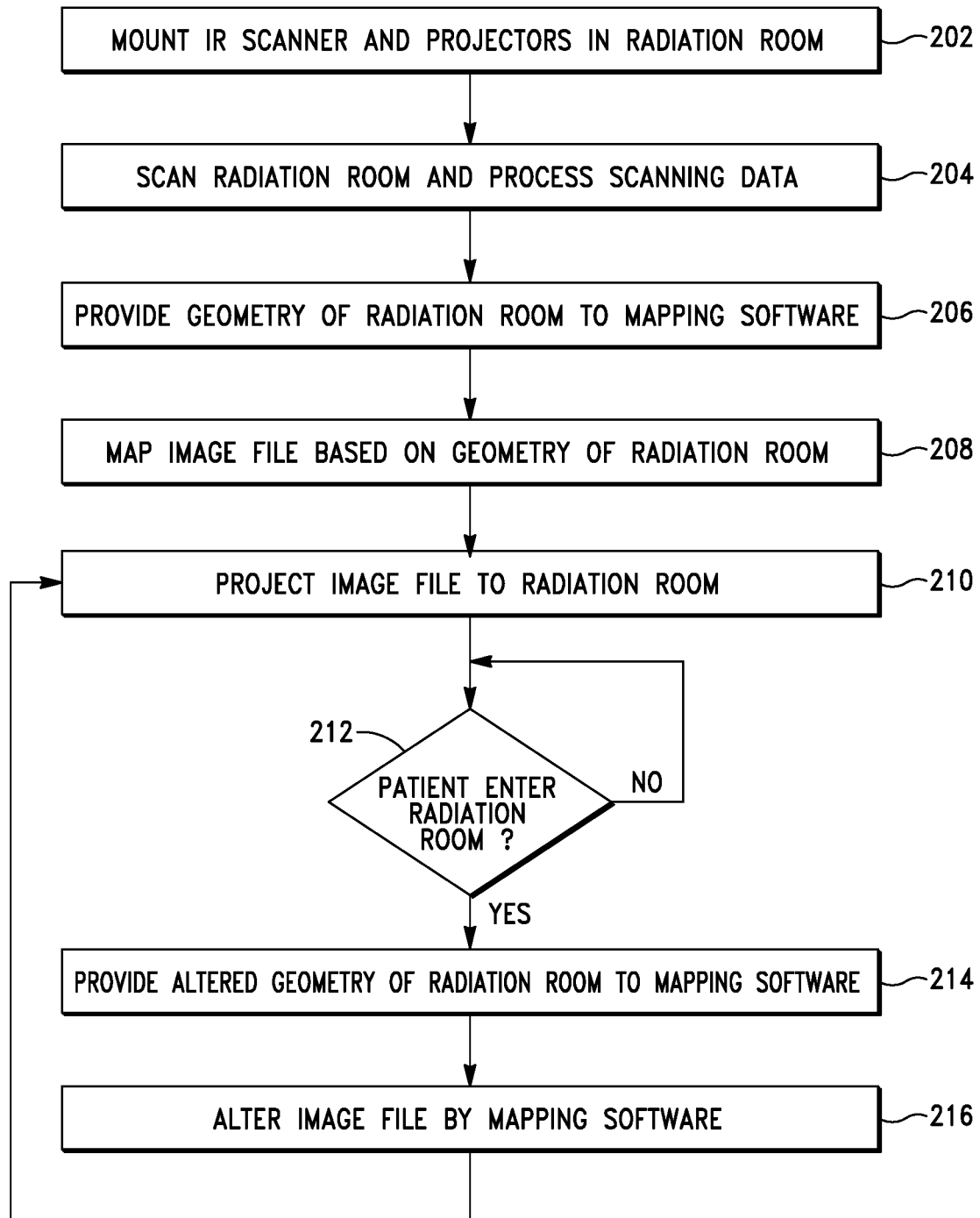
FIG. 2 is a flowchart illustrating an exemplary method for mapping and projecting images to a radiation suite according to embodiments of the disclosure.

FIG. 2 is a flowchart illustrating an exemplary method for projection mapping a radiation suite according to some embodiments of the disclosure. The method is described herein in conjunction with FIG. 1 which depicts a radiation system 140 in a radiation room 120. It will be appreciated by one of ordinary skill in the art that the method can also be implemented in other medical facilities, such as a surgical room without a radiation system or a doctor's office, to provide a calming environment. According to the method, one or more scanners 162, and one or more projectors 164 are mounted in a radiation room 120 (step 202). The one or more projectors 164 may be mounted on the side walls 126 adjacent to an entrance to the radiation room 120 so that images are projected or displayed on the radiation system 142 generally in the viewpoint of the patient entering the room. The projectors 164 may also be mounted in other suitable locations such as on the ceiling 124 and/or the floor 122 of the room 120. Other considerations for projectors' mounting locations include the existence of an optical path between the projectors and the surfaces onto which images are to be projected. The locations of the projectors may also depend on the contents of the images that have been produced. In some embodiments, the image file may be custom-produced after the projectors are mounted at selected locations. If desired, multiple projectors may be mounted to cover the entire radiation room.

At step 204, one or more scanners 162 operate to scan the room 120, including the floor 122, ceiling 124, walls 126, the radiation system 140 and other objects in the room 120. The scanning data is sent to a computer 170, which runs a scanning software 176 processing the scanning data to determine the contour or geometry of the radiation room 120 and the radiation system 140, and their coordinates in relation to the projectors 164.

At step 206, the computer 170 provides information about the geometry of the room 120 and the radiation system 140 to a projection mapping software 171. The projection mapping software 171 functions to map an image file to a selected surface or the entire surface of the radiation system 140 and/or the room 120 by e.g. warping, masking, edging and/or other means provided by the mapping software until the projected image matches the geometry and contour of the projection surface (step 208). One example of projection mapping software is MadMapper®. The mapped image file may be stored in the memory of the computer 170. The mapped image file can be fed to the projectors 164 and projected to the selected surface or entire surface of the radiation system 140 and the room 120 (step 210). Alternatively, the mapped image file may be saved in a memory device such as a CD, USB drive, or the like, which can be inserted into a port in the projectors for projection.

The entry of a patient may change the geometry or the projection surface of the radiation room (step 212). The movement of the patient may be detected or tracked in real time by the scanner 162 and the scanning software 176 run in the computer 170. The computer 170 provides information about the movement of the patient or the change of geometry of the radiation room caused by the patient's movement to the projection mapping software 171 (step 214). In response to the change of geometry of the radiation room 120, the mapping software 171 may alter the image file e.g. by intermixing another image file to create a composite image file (step 216). The altered image file is projected to the radiation room 120 including the radiation system 140 (step 210), creating a dynamic interaction between the patient and the augmented reality.

Figure 3A:
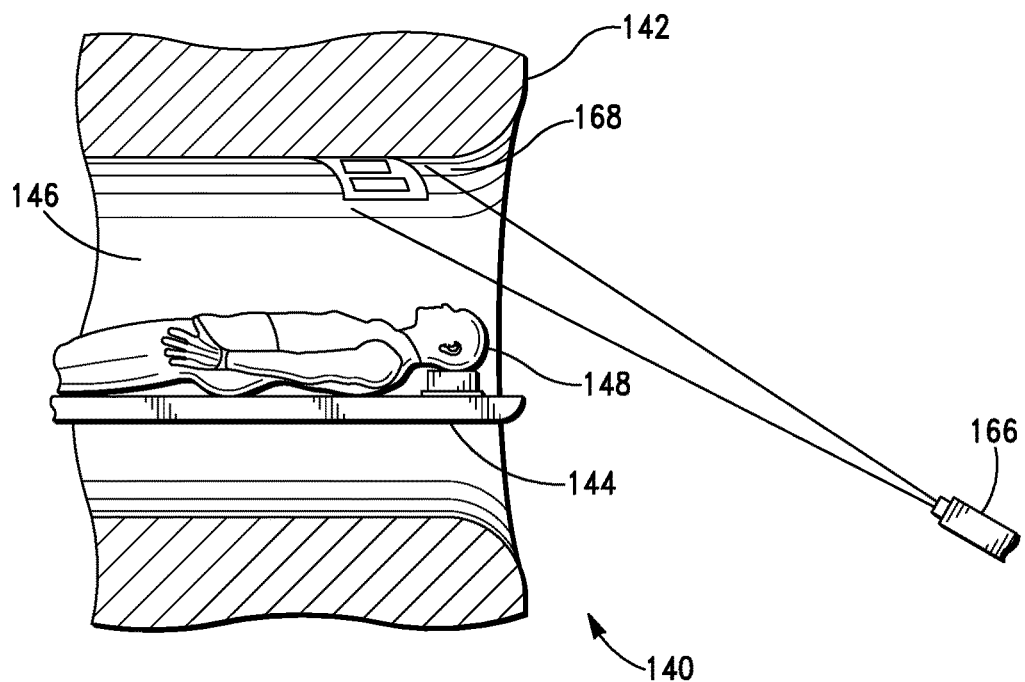
FIGS. 3A and 3B illustrate an exemplary embodiment projecting an image on a surface of a bore of a ring gantry according to embodiments of the disclosure.
Figure 3B:
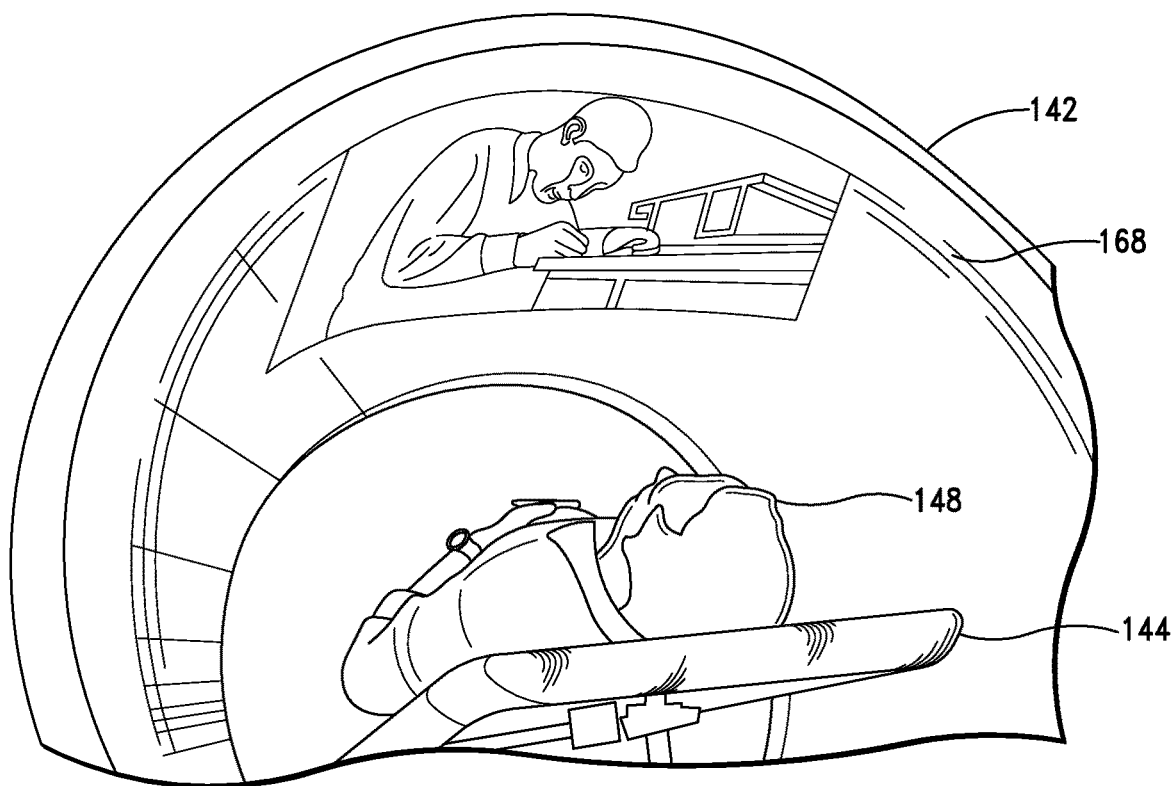

Referring to FIGS. 3A and 3B, an alternative embodiment of the disclosure will now be described. FIGS. 3A and 3B show a radiation system 140, which may be located in a radiation suite 100 comprising an image projection system 160 as described above in connection with FIG. 1. The radiation system 140 comprises a ring gantry 142 enclosing a radiation source (not shown) and a couch 144 supporting a patient 148. The ring gantry 142 may include a bore 146 for receiving at least a portion of the patient 148. In addition to the projectors 164 described above in connection with the image projection system 160 shown in FIG. 1, an additional projector 166 may be mounted in the room 120 to project an image file to the surface 168 defining the bore 146, allowing the patient 148 lying on the couch 144 to watch during treatment or imaging. The projector 166 may project an image file in the direction of the patient's viewpoint during treatment or imaging since this is the position the patient 148 remains in for the longest time.

The projector 166 may be mounted on the wall or floor, and operably connected with and controlled by the computer 170. The image file may be mapped to the bore surface 168, which may be curved, using the mapping software 171 run by the computer 170 as described above. The image file may be adapted for relaxing the patient 148. By way of example, for pediatric patients, images of animals, birds, fish, or space etc. or a cartoon movie may be projected on the surface 168 to distract children from their treatment or imaging by the radiation machine.

Alternatively, the image file projected by the projector 166 may be adapted for visual gating learning and feedback during treatment or imaging. Therefore, according to embodiments of the disclosure, the projector 166 or the image projection system 160 may be operably connected with a gating system (not shown in FIGS. 3A and 3B) provided with the radiation system 140. To irradiate a target or tumor that is not stationary, "gating" is normally utilized to block the radiation beam whenever the tumor is out of position. A gating system may include an imaging device such as an infrared camera continuously tracking one or more motion surrogates such as markers, implanted sensors or the like directly correlated to the motion and/or position of the tumor. A computer processes the signals from the surrogates to correlate the motion of the surrogates with the motion or position of the tumor in real time, and generate gating signals synchronized to the motion of the tumor to the control of the radiation system. According to embodiments of the disclosure, the projector 166 may project an image file to the bore surface 168 that prompts the patient 148 to maintain a desired physiological movement pattern. For example, a slider image or a graphical signal chart that simultaneously displays visual feedback of the physiological movement of the patient and a desired range or window of the movement can be projected. For respiration activity, the slider or the graphical signal chart may include a movable bar or other suitable symbol that moves in response to the patient's inhale-exhale movements. This provides visual prompting and feedback regarding the respiration activity. Verbal prompting may be employed in conjunction with the visual prompting to assist in controlling, maintaining, or manipulating the physiological activity of interest. Such verbal promptings can be computer-activated promptings to instruct a patient to breath in and breath out. U.S. Pat. No. 9,232,928 B2 entitled "Method and System for Predictive Physiological Gating" describes various embodiments of patient feedback and visual gating learning, the disclosure of all of which is incorporated herein by reference in its entirety.

Embodiments of projection mapping a radiation suite have been described. Those skilled in the art will appreciate that various other modifications may be made within the spirit and scope of the invention. All these or other variations and modifications are contemplated by the inventors and within the scope of the invention.

What is claimed is:

1. A method for use in a radiation suite including a radiation system and an image projection system, the radiation system including one or more surfaces constituting a projection surface and a gating system, the method comprising:
   providing an image containing content adapted to prompt a patient to maintain a desired physiological movement pattern;
   positioning the patient on a supporting device to allow the patient to view the projection surface;
   projecting the image to the projection surface to prompt the patient to maintain the desired physiological movement pattern; and
   synchronizing the projecting of the image to the projection surface to the gating system.

2. The method of claim 1, wherein the radiation system comprises a ring gantry having a bore configured to receive at least a portion of the patient on the supporting device, wherein the bore of the ring gantry is defined by a surface comprising the projection surface.

3. The method of claim 2, wherein the image projected on the projection surface further comprises a visual feedback of a physiological movement of the patient.

4. The method of claim 3, wherein the visual feedback of the physiological movement of the patient and the desired physiological movement pattern are respectively represented by a moving graph or symbol.

5. The method of claim 3, wherein the visual feedback of the physiological movement of the patient and the desired physiological movement pattern comprise respiration activity of the patient.

6. The method of claim 1, further comprising providing audible instruction to the patient while the image is projected to the projection surface to prompt the patient to maintain the desired physiological movement pattern.

7. The method of claim 1, wherein the gating system comprises an imaging device and a motion surrogate device in or on the patient correlating to motion of a target in the patient, the imaging device tracking the motion surrogate device allowing for generating a gating signal synchronized to the motion of the target and providing the gating signal to the image projection system.

8. The method of claim 7, wherein the gating signal correlates to respiration activity of the patient.

9. The method of claim 8, wherein the projecting of the image comprises a visual feedback of the respiration activity of the patient and a desired respiration activity pattern for the patient.

10. The method of claim 9, wherein the visual feedback of the respiration activity of the patient and the desired respiration activity pattern for the patient are respectively represented by a moving graph or symbol.

11. A radiation suite, comprising:
   a room;
   a radiation system including a radiation source enclosed in a gantry, the gantry including one or more surfaces, at least a portion of the one or more surfaces forming a projection surface;
   a gating system; and
   an image projection system operable to project an image to the projection surface on the radiation system, wherein the image projection system is synchronized to the gating system and includes a computer and a first projector, the computer including a first image containing content adapted to prompt a patient to maintain a desired physiological movement pattern, and the first projector being operable to project the first image to the projection surface in synchronization with a gating signal from the gating system.

12. The radiation suite of claim 11, wherein the gantry comprises a ring gantry having a bore having an inner surface and configured to receive at least a portion of the patient, wherein the inner surface comprises the projection surface.

13. The radiation suite of claim 11, wherein the desired physiological movement pattern comprises respiration activity.

14. The radiation suite of claim 11, wherein the desired physiological movement pattern is represented by a moving graph or symbol.

15. The radiation suite of claim 11, wherein the gating system comprises an imaging device and a motion surrogate device in or on the patient correlating to motion of a target in the patient, the imaging device tracking the motion surrogate device allowing for generating the gating signal synchronized to the motion of the target and providing the gating signal to the image projection system.

16. The radiation suite of claim 11, wherein the computer further comprises a second image containing content suitable for calming the patient and a mapping software operable to map a second image to the projection surface, and the first projector is operable to project the mapped second image to the projection surface.

17. The radiation suite of claim 16, wherein the gantry of the radiation system is generally C-shaped and rotatable about a horizontal axis.

18. The radiation suite of claim 17, further comprising a scanner and scanning software run in the computer operable to detect motion of the gantry, wherein the mapping software is operable to dynamically alter the second image in response to a change of the projection surface caused by the motion of the gantry.

* * * * *